(12) United States Patent
Weber et al.

(10) Patent No.: US 6,194,456 B1
(45) Date of Patent: Feb. 27, 2001

(54) METHOD FOR INHIBITING INFLAMMATION

(75) Inventors: Carsten Weber, Jena; Ralf Oettmeir; Uwe Reuter, both of Greiz, all of (DE)

(73) Assignee: Medicur Pharma GmbH, Jena (DE)

( * ) Notice: Subject to any disclaimer, the term of this patent is extended or adjusted under 35 U.S.C. 154(b) by 0 days.

(21) Appl. No.: 09/171,380

(22) PCT Filed: Mar. 25, 1998

(86) PCT No.: PCT/EP98/01742

§ 371 Date: Oct. 16, 1998

§ 102(e) Date: Oct. 16, 1998

(87) PCT Pub. No.: WO98/43633

PCT Pub. Date: Oct. 8, 1998

(30) Foreign Application Priority Data

Mar. 29, 1997 (DE) .............................. 197 13 263

(51) Int. Cl.[7] .......................... A61K 31/24; A61K 33/14; A61K 33/00
(52) U.S. Cl. .......................... 514/535; 424/680; 424/717
(58) Field of Search .................. 514/535; 424/680, 424/717

(56) References Cited

U.S. PATENT DOCUMENTS

| | | | |
|---|---|---|---|
| 4,748,022 | 5/1988 | Busciglio | 424/195.1 |
| 5,149,320 | * 9/1992 | Dhaliwal et al. | 604/49 |
| 5,209,724 | 5/1993 | Dhaliwal et al. | 604/49 |
| 5,505,922 | * 4/1996 | Thut et al. | 424/677 |
| 5,580,901 | 12/1996 | Boardman et al. | 514/536 |

FOREIGN PATENT DOCUMENTS

| | | |
|---|---|---|
| 2 704 429 | 11/1994 | (FR) . |
| 75725 | * 2/1981 | (RO) . |

OTHER PUBLICATIONS

XP–002068518 / Journal of Pharmaceutical Sciences, Oct. 10, 1975, pp. 1713–1715 "Activity of Local Anesthetic Agents in Goldfish" Feldman, et al.

XP–002068519 / Aquaculture, 1994, pp. 1994, pp. 395–398, "The Use of Lidocaine–sodium Bicarbonate as Anaesthetic in Fish" Carrasco, et al.

XP–002068520 / Martindale–The Extra Pharmacopoeia 31 Edition, 1996, Royal Pharmaceutical Society London, p. 1320 "Intravenous Analgesia" R. Jef.

* cited by examiner

*Primary Examiner*—Kevin E. Weddington
(74) *Attorney, Agent, or Firm*—Reed Smith LLP

(57) ABSTRACT

A drug which is preferably usable for inhibiting inflammation in chronic and autoimmune inflammatory processes and/or produces vasodilating and sympathicolytic effects.

This use is achieved through a drug from a mixture containing a local anesthetic of the ester type or amide type, preferably procaine hydrochloride, water, and at least one substance for adjusting the pH of the mixture in the range of 7.6 to 8.6. It is possible by this drug to significantly increase the injectable amount of local anesthetic compared with commercially available and known drugs containing a local anesthetic as active ingredient. The mixture can be applied continuously by subcutaneous or intravenous infusion.

4 Claims, No Drawings

METHOD FOR INHIBITING INFLAMMATION

BACKGROUND OF THE INVENTION a) Field of the Invention

The invention is directed to a drug which is preferably usable for inhibiting inflammation in chronic and autoimmune inflammatory processes and/or produces vasodilating and sympathicolytic effects.

b) Description of the Related Art

The pharmacological characteristics of ester type and amide type local anesthetics are well known. Procaine hydrochloride (Procaine, Procaine-N-glucoside-hydrochloride, chemical designation: 2-diethylaminoethyl-4-aminobenzoate) is a basic ester type local anesthetic; it inhibits the function of excitable structures such as sensory, motor and autonomic nerve fibers, influences the stimulus conduction of the heart, and is applied clinically for local and regional nerve blockade.

Procaine hydrochloride cancels the conduction capacity of the sensory nerve fibers in a reversible and locally delimited manner. After reducing sensitivity to pain, in descending order, sensitivity to cold or heat, touch and pressure are reduced. Procaine hydrochloride acts on smooth muscles as an antiarrhythmatic and tone reducer. Further, it has a mild antihistaminic and parasympatholytic effect.

The action of procaine hydrochloride is known to the extent that procaine hydrochloride reduces membrane permeability to cations, especially to sodium ions and, in higher concentrations, also potassium ions. Because of this, a reduced excitability of nerve fibers can be achieved, depending on the concentration, because the sudden rise in sodium permeability necessary for the development of action potential is reduced. Membrane stabilization is based on the storing of lipophilic local anesthetics in the cellular membrane, so that ion channels, especially sodium channels, are blocked.

However, it is also known that the resorption of local anesthetics, and therefore also the resorption of procaine hydrochloride, is problematic and their usefulness is therefore limited. The resorption of procaine hydrochloride depends on the vascularization and blood flow at the site of injection, insofar as procaine hydrochloride is administered by injection. The latent period prior to the onset of action is 1–2 minutes in the case of infiltration and 15–20 minutes in the case of epidural anesthesia. The duration of action is 1–2 hours. In general, due to the low resorbability of procaine hydrochloride, only the smallest dose by which the desired adequate nerve blockade can be achieved may be administered. Dosage is determined on the basis of the peculiarities of the individual case (see the monograph "Procaine as Injection Solution", published in the German Federal Gazette No. 144 of 8/3/1994, Bundesinstitut fur Arzneimittel and Medizinprodukte). It is recommended herein that, when applied in tissues from which a rapid resorption of substances is carried out, an individual dose may not exceed 500 mg of procaine hydrochloride without addition of vasoconstrictors or 600 mg of procaine hydrochloride with addition of vasoconstrictors. Numerous additional precautionary indications must be taken into consideration. In this connection, its high osmolarity is of 290 mOsmol and the low pH between 4.0 and 6.0 are disadvantageous.

As a result, it was formerly supposed that procaine hydrochloride is not suitable for continuous application. When administered in the conventional manner, pain, redness, heat buildup and swelling occur at the injection site within a short period following injection. When injected subcutaneously, liquid chambers occur 20 along with the above-mentioned complaints, likewise as a result of the insufficient resorption rate for procaine hydrochloride in the subcutaneous tissue. When injected in peripheral veins, thrombophlebitic complications develop in addition after about 48 hours.

The anti-inflammatory action of procaine hydrochloride is also known. However, it has not been possible so far to take advantage of the full potential of this anti-inflammatory action with the current maximum possible dosages and discontinuous administration. Although it has long been desirable to administer procaine hydrochloride in large doses and in a continuous manner in order to permit the development of this action, it is still assumed by those skilled in the art that continuous injection of procaine hydrochloride is impossible in view of the described side effects, limitations and risks.

It has been attempted to administer procaine amide orally in the form of tablets or capsules, but this method is difficult to control because of broad individual tolerances of the resorption rates. In view of this uncertainty, the pronounced effect of procaine hydrochloride on the stimulus conduction of the cardiac muscle results in corresponding risks. It follows, inversely, that safe application presupposes good controllability of the active ingredients level.

OBJECT AND SUMMARY OF THE INVENTION

According to the invention, this object is met through a drug from a mixture containing at least one local anesthetic of the ester type or amide type, water, and at least one substance for adjusting the pH of the mixture in the range of 7.6 to 8.6. It is possible by means of this drug to significantly increase the injectable amount compared with commercially available and known drugs containing a local anesthetic as active ingredient. The mixture can be applied continuously by subcutaneous or intravenous injection. In comparison to previously available possibilities, a decisive increase in the daily dosage can be achieved, resulting in the potentiation of the strength and duration of action especially with respect to the development of potential for anti-inflammatory effects. Also, the undesirable side effects such as pain, redness, heat buildup, etc. do not occur when the daily dosage or duration of injection are increased.

A particularly preferred embodiment of the invention provides procaine hydrochloride as local anesthetic. In further embodiments, the following can be provided as local anesthetics: lidocaine, bupivacaine, mepivacaine, benzocaine, cocaine, butacaine, tetracaine, isocaine, proparacaine, metabutoxycaine, prilocaine, pyrocaine, dibucaine, piridocaine and/or eucaine.

It has therefore been shown surprisingly that local anesthetics administered within this mixture have a substantially higher resorption rate. Procaine hydrochloride in particular can now be applied in substantially greater scope with extremely positive results for blocking inflammations, especially of chronic and autoimmune inflammatory processes. A very promising possibility of application is for the treatment of chronic spondylitis until the decay of the illness can no longer be detected by bone scintigraphy. The advantageous effect appears to be based on a heretofore unknown influence on the immune system, especially on T lymphocytes and B lymphocytes.

Another substantial advantage consists in that the increased resorption rate can be well and reliably controlled, so that the influence on the stimulus conduction at the cardiac muscle and the related risk can be monitored in a very favorable manner because the serum concentration is directly proportional to the dosage.

In a clinical test based on n=400 injections, the pH range of 7.2 to 7.6 of a first group and the pH range of 7.8 to 8.6 in a second group were compared. In the first group, redness, swelling and sometimes burning pain occurred in every case over an injection period of 24 hours. In the second group, none of the above-mentioned side effects occurred.

In an embodiment of the invention, sodium bicarbonate is provided as means for adjusting the pH. The mixture can contain 1.8 parts by weight of sodium bicarbonate for every part by weight of procaine hydrochloride. Accordingly, a resorption rate can be achieved which, under normal circumstances, enables a long-term application at increased daily doses without risk and, in so doing, develops in particular the anti-inflammatory action of procaine hydrochloride.

DESCRIPTION OF THE PREFERRED EMBODIMENT

It can be provided in an advantageous manner that the mixture contains 45 to 70 parts by weight of water for every part by weight of procaine hydrochloride. This enables subcutaneous or intravenous injection of the drug with good results.

Within the framework of this embodiment, a mixture can contain 1.3 parts by weight of sodium bicarbonate and 60 parts by weight of water for every part by weight of procaine hydrochloride. The values mentioned above for inflammation parameters from blood analyses of a plurality of patients accordingly show optimum results.

In a particularly preferred embodiment of the invention, the mixture has an osmolarity of less than 240 mOsmol. The adjustment of the osmolarity of the mixture according to the invention is carried out by varying the proportion of water.

In another very preferable embodiment of the invention, sodium chloride is contained in the mixture. By adding sodium chloride and varying its content, it is possible to control the volume of the drug in a very advantageous manner in accordance with the practical requirements of medical application.

The drug mixture can contain 1.3 parts by weight of sodium bicarbonate, 60 parts by weight of water, and 0.9 parts by weight of sodium chloride for every part by weight of procaine hydrochloride. In this way, excellent results can be achieved above all in the treatment of rheumatic illnesses with long-term application at increased daily doses.

In further developments of the invention, the mixture can contain additional conventional carriers, auxiliary substances, added ingredients and/or stabilizers.

The invention is further directed to the use of the above-described mixture for inhibition of inflammation in chronic and autoimmune inflammatory processes and/or for achieving vasodilating and sympathicolytic actions. In this respect, it is provided in a use embodiment that the drug is administered by injection over a period of at least 24 hours.

In a particularly preferred manner, the mixture is administered over the total infusion period with constant infusion amounts. The infusion quantity is advantageously maintained constant by an infusion pump.

Surprisingly, when used in the manner described above, the anti-inflammatory action of procaine hydrochloride can be utilized therapeutically.

EMBODIMENT EXAMPLE

The invention will be described hereinafter with reference to an embodiment example. For example, the drug is a mixture of:

| | |
|---|---|
| 60 ml | procaine hydrochloride solution, 2 percent |
| 60 ml | water up to injections |
| 20 ml | sodium bicarbonate solution, 8.4 percent, and |
| 110 ml | sodium chloride solution, 0.9 percent. |

The ingredients are mixed and are applied by subcutaneous or intravenous infusion over a period of 24 hours.

While the foregoing description represents the present invention, it will be obvious to those skilled in the art that various changes may be made therein without departing from the true spirit and scope of the present invention.

What is claimed is:

1. A method for using a mixture with the following components:
   at least one local anesthetic of the ester type or amide type,
   water, and
   at least one substance for adjusting the pH of the mixture in the range of 7.6 to 8.6
comprising the step of using said mixture for continuous application for inhibition of inflammation in chronic and autoimmune inflammatory processes and/or for achieving vasodilating and sympathicolytic actions.

2. The method according to claim 1, wherein administration is carried out by infusion over a period of at least 24 hours.

3. The method according to claim 2, wherein administration is carried out over the total infusion period with constant infusion amounts.

4. The method according to claim 3, wherein the infusion quantity is maintained constant by an infusion pump.

\* \* \* \* \*